US00PP29373P3

(12) United States Plant Patent
Pan

(10) Patent No.: US PP29,373 P3
(45) Date of Patent: Jun. 12, 2018

(54) ***LANTANA* PLANT NAMED 'LANZ0013'**

(50) Latin Name: ***Lantana camara* L.**
Varietal Denomination: LANZ0013

(71) Applicant: SYNGENTA PARTICIPATIONS AG, Basel (CH)

(72) Inventor: Shifeng Pan, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days. days.

(21) Appl. No.: 14/999,740

(22) Filed: Jun. 21, 2016

(65) Prior Publication Data

US 2017/0339809 P1 Nov. 23, 2017

(30) Foreign Application Priority Data

May 23, 2016 (QZ) ..... PBR 2016/1238

(51) Int. Cl.
*A01H 5/02* (2018.01)

(52) U.S. Cl.
USPC ..... Plt./227
CPC ..... *A01H 5/02* (2013.01)

(58) Field of Classification Search
USPC ..... Plt./226, 227
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new *Lantana* plant named 'LANZ0013' particularly distinguished by the large sized tri-colored, golden, orange and scarlet red flowers, excellent floriferousness, and dense mounding habit with medium green foliage.

1 Drawing Sheet

Latin name of the genus and species of the plant claimed: *Lantana camara* L.

Varietal denomination: 'LANZ0013'.

BACKGROUND OF THE NEW PLANT

The present invention comprises a new *Lantana*, botanically known as *Lantana camara* L., and hereinafter referred to by the variety name 'LANZ0013'.

'LANZ0013' is a product of a planned breeding program. The new cultivar 'LANZ0013' has large sized tri-color, golden, orange and scarlet red flowers, excellent floriferousness, and uniform compact and dense mounding habit with medium green foliage.

'LANZ0013' originates from an open hybridization in an outdoor field in July 2011 in Gilroy, Calif., USA. The female parent was an unpatented, proprietary plant identified as 'LEC0669-2', with cherry flower color, a more compact plant habit, and faster flowering response when compared to 'LANZ0013'. The male parent is unknown.

The seed was sown in December 2011 in a greenhouse in Gilroy, Calif. and 'LANZ0013' was selected as one flowering plant within the progeny of the stated cross in February 2012.

The first act of asexual reproduction of 'LANZ0013' was accomplished when vegetative cuttings were propagated from the initial selection in June 2012 in a greenhouse in Gilroy, Calif.

BRIEF SUMMARY OF INVENTION

Horticultural examination of plants grown from cuttings of the plant initiated in June 2012, in Gilroy, Calif., and continuing thereafter, has demonstrated that the combination of characteristics as herein disclosed for 'LANZ0013' are firmly fixed and are retained through successive generations of asexual reproduction.

'LANZ0013' has not been observed under all possible environmental conditions. The phenotype may vary significantly with variations in environment such as temperature, light intensity, and day length.

A Plant Breeder's Right for this cultivar was applied for in the European Union on May 23, 2016, No. 2016/1238. 'LANZ0013' has not been made publicly available prior to the effective filing date of this application, notwithstanding any disclosure that may have been made less than one year prior to the effective filing date of this application by the inventor or another who obtained 'LANZ0013' directly from the inventor.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

Figure 1:
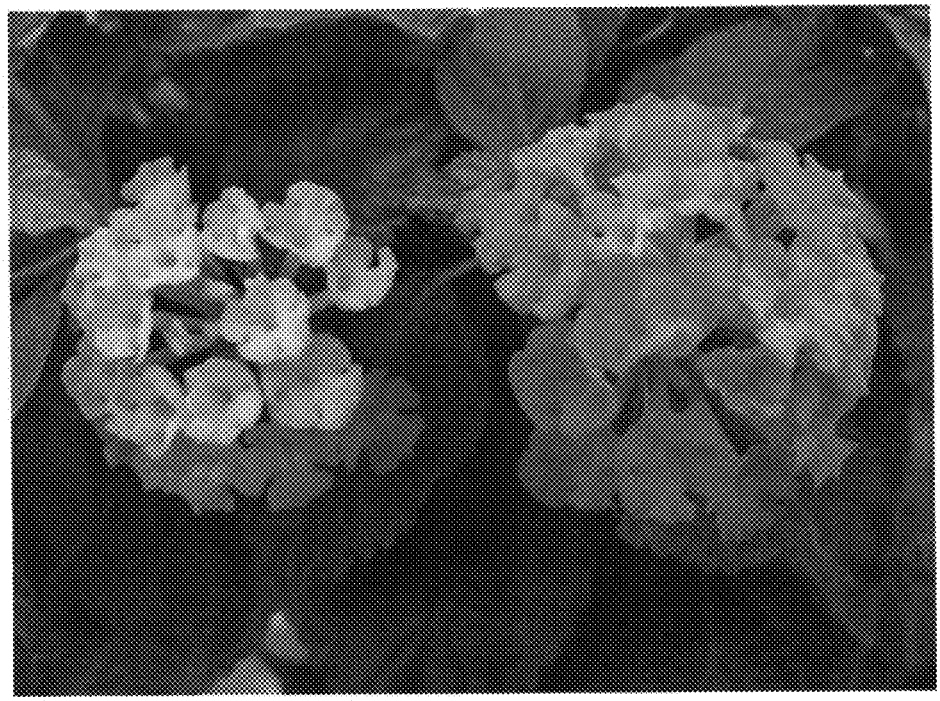
Figure 2:
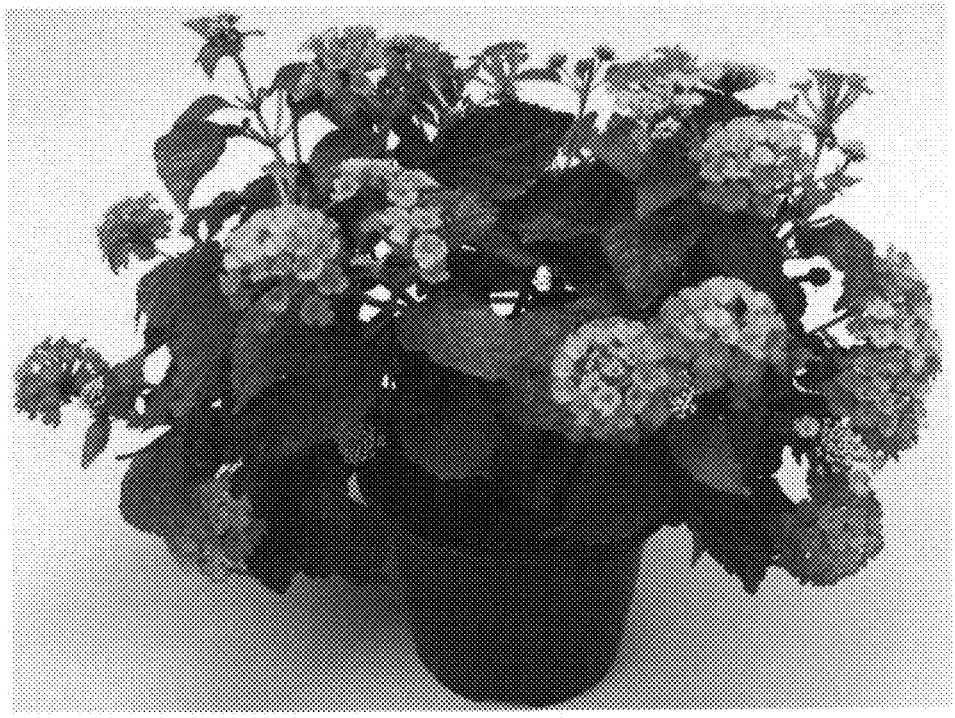

The accompanying photographic drawings show typical flower and foliage characteristics of 'LANZ0013' with colors being as true as possible with an illustration of this type. The photographic drawings show in FIG. 1 a close view of an inflorescence, and in FIG. 2 a whole flowering plant.

DETAILED BOTANICAL DESCRIPTION

The plant descriptions and measurements were taken in Gilroy, Calif. in May 2016. The plants were approximately 3.5 months old and were growing in quart size pots in a greenhouse.

The aforementioned photographs show those same plants as used for the description were taken in Gilroy, Calif. on May 16, 2016 and show 3.5 month old plants from an indoor trial.

Color references are made to The Royal Horticultural Society Colour Chart (R.H.S.) 2001.

TABLE 1

DIFFERENCES BETWEEN THE NEW VARIETY 'LANZ0013' AND A MOST SIMILAR VARIETY

| | 'LANZ0013' | 'Balluced' (PPAF) |
|---|---|---|
| Floret size: | Larger | Smaller |
| Inflorescence, diameter: | Larger | Smaller |
| Plant height/diameter: | Taller growth | Lower growing |

Plant:

*Form, growth and habit.*—Semi-woody, grown as an annual or perennial; compact and dense mounding habit; very well branched.

*Plant height.*—12-13.0 cm.

*Plant height* (*inflorescence included*).—14-16.0 cm.

*Plant width.*—22-29.0 cm.

Foliage:

*Type.*—Opposite.

*Immature, leaf color, upper surface.*—RHS 137B.

*Lower surface.*—Closest to RHS 137C.

*Mature, leaf color, upper surface.*—RHS 137A.

*Lower surface.*—Closest to RHS 137C.

*Length.*—7.0-7.8 cm.

*Width.*—4.9-5.6 cm.

*Shape.*—Ovate.

*Base shape.*—Attenuate.

*Apex shape.*—Acute.

*Margin.*—Dentate.

*Texture, upper surface.*—Hirsute.

*Texture, lower surface.*—Hirsute.

*Pattern of veining.*—Pinnate.

*Petioles color.*—RHS 137B.

*Petioles length.*—1.8-3.0 cm.

*Diameter of petiole.*—0.2 cm.

*Texture* (*upper and lower surface*).—Hirsute with some very short glandular hairs.

Stem:

*Color of stem.*—RHS 147D.

*Length of stem.*—9-14.0 cm.

*Diameter.*—2-2.5 cm.

*Length of internodes.*—2.2-3.0 cm.

*Texture.*—Pilose, hirsute.

Inflorescence:

*Type.*—Umbel like, flattened semi-sphere the florets are sessile on an ovate receptacle.

*Blooming habit.*—Flowers continuously from spring through fall.

*Number of open flowers per inflorescence.*—26-34.

*Quantity of inflorescences per plant.*—About 24 (with open florets).

*Lastingness of individual blooms on the plant.*—About 4 weeks (depending on temperatures).

*Fragrance.*—Slightly spicy.

*Umbel horizontal diameter.*—About 3.8 cm.

*Umbel vertical height.*—2.0-2.0 cm.

*Peduncle color.*—RHS 147D.

*Length of peduncle.*—2.2-3.0 cm.

*Peduncle diameter.*—0.15 cm.

*Texture.*—Hirsute, glandular hairs.

Flower:

*Floret form.*—Corolla salver-shaped to shallow cup-shaped, with a relatively long tube at the base; each flower subtended by a single bract.

*Length of floret.*—1.0-1.2 cm.

*Width of floret.*—0.9-1.0 cm.

*Depth of floret.*—1.7 cm.

*Young floret, color upper surface.*—RHS 13A lightly overlain with RHS 23B.

*Young floret, color lower surface.*—RHS 8B and RHS 24B.

*Mature florets, color upper surface.*—RHS 45A with RHS 23A throat.

*Mature floret, color lower surface.*—RHS 12D and RHS 179C.

*Apex shape.*—Slightly mucronulate.

*Degree of lobation.*—Moderate.

*Margin.*—Entire.

*Base.*—Fused.

*Texture, upper surface.*—Papillose.

*Lower surface.*—Papillose.

*Tube, color outer surface.*—Closest to RHS 12D and RHS 179C.

*Tube, color inner surface.*—Closest to RHS 163C.

*Tube, length.*—1 cm.

*Tube, diameter* (*at opening*).—0.2 cm.

*Tube, texture outer surface.*—Pubescent.

*Inner surface.*—Hirsute.

Bud (just before opening):

*Color.*—RHS 12C.

*Length.*—1.3 cm.

*Width.*—0.3-0.4 cm at the apex.

*Shape.*—Tubular with a flared apex.

Bract:

*Color.*—Closest to RHS 138A with a RHS 137B apex.

*Length.*—0.5-0.6 cm.

*Diameter.*—0.2 cm.

*Texture, upper surface.*—Hirsute.

*Lower surface.*—Hirsute.

Calyx:

*Number of sepals.*—5, fused sepals forming a short tube around the base of the floret.

*Color of sepals.*—RHS 138A.

*Length of sepals.*—0.5-0.6 cm.

*Width of sepals.*—0.15 cm.

*Apex shape.*—Obtuse.

*Apex Margins.*—Entire.

*Texture, outer surface.*—Pubescent.

*Inner surface.*—Glabrous.

Reproductive organs:

*Gynoecium.*—

*Pistil quantity.*—One.

*Length.*—0.35 cm.

*Style color.*—RHS 159D.

*Style length.*—0.2 cm.

*Stigma color.*—RHS 144B.

*Ovary color.*—RHS 144A.

*Ovary length.*—0.1 cm.

*Ovary diameter.*—0.05 cm

*Androecium.*—

*Stamen quantity.*—4.

*Color of filaments.*—RHS 159D

*Length filaments.*—0.05 cm.

*Anther color.*—RHS 164A.

*Length of anthers.*—0.1 cm.
*Color of pollen.*—RHS 10D.
*Pollen amount.*—Normal.
*Fertility/seed set.*—Has not been determined to date.
*Disease/pest resistance.*—Has not been determined to date.

What is claimed is:

1. A new and distinct variety of *Lantana* plant named 'LANZ0013' substantially as illustrated and described herein.

* * * * *